Figure 1A:
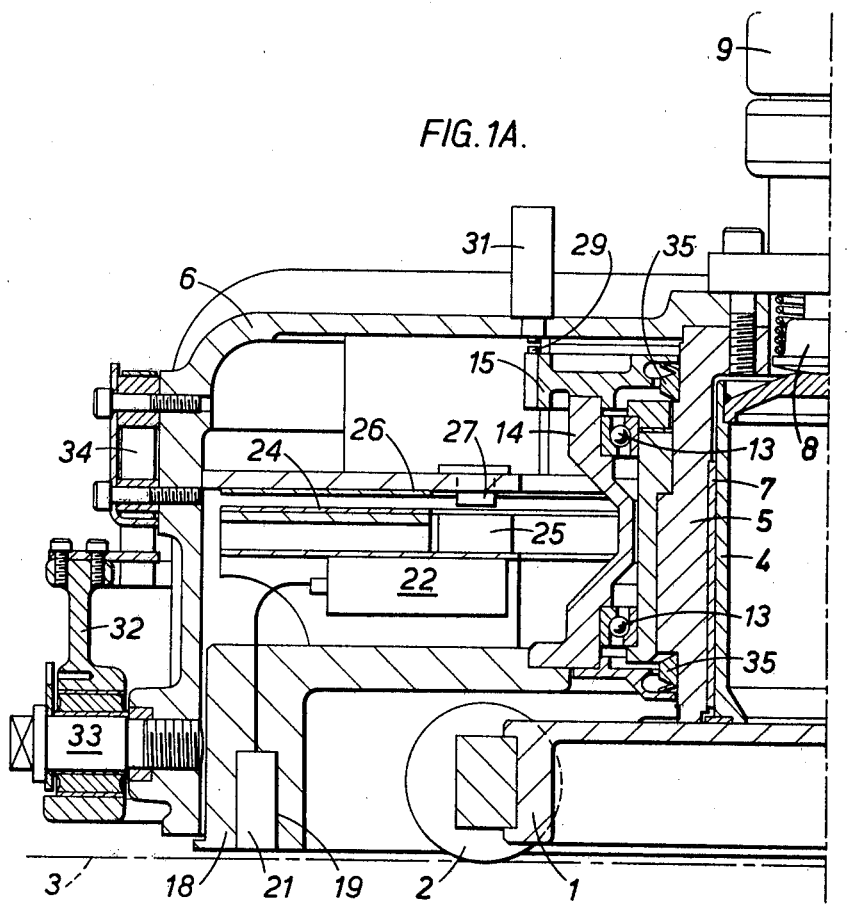

United States Patent [19]

Garner et al.

[11] 4,409,549
[45] Oct. 11, 1983

[54] CARRIAGE MOUNTED APPARATUS FOR DETECTING SURFACE DEFECTS IN FLAT SURFACED METALLIC OBJECTS

[75] Inventors: Henry C. Garner, Swinton; Jack Broadbent, Rotherham; David H. Savidge, Rotherham; Eric Wadsworth, Dinnington, all of England

[73] Assignee: British Steel Corporation, London, England

[21] Appl. No.: 226,638

[22] Filed: Jan. 21, 1981

[30] Foreign Application Priority Data

Jan. 29, 1980 [GB] United Kingdom ................ 8002887

[51] Int. Cl.³ ...................... G01N 27/90; G01R 33/12
[52] U.S. Cl. .................................................. 324/262
[58] Field of Search ........ 324/227, 228, 232, 234–240, 324/262, 226

[56] References Cited

U.S. PATENT DOCUMENTS 3,109,139 10/1963 Branker ................................ 324/240
3,449,664 6/1969 Smith .................................... 324/235
3,974,442 8/1976 Savidge et al. ........................ 324/37

FOREIGN PATENT DOCUMENTS 2008259 5/1979 United Kingdom .

Primary Examiner—Gerard R. Strecker
Attorney, Agent, or Firm—Bacon & Thomas

[57] ABSTRACT

The invention concerns apparatus for inspecting the flat surfaces of a metal billet and includes a carriage mounted scanning head having a high frequency eddy-current probe (21) mounted on the periphery of a disc (18) rotatable above the billet surface about an axis perpendicular to said surface. The carriage (1) is located in abroad of the rotating scanning head. The eddy-current probe is connected to transmit electrical signals representative of the condition of the billet surface under inspection to signal processing equipment remote from the apparatus.

2 Claims, 2 Drawing Figures

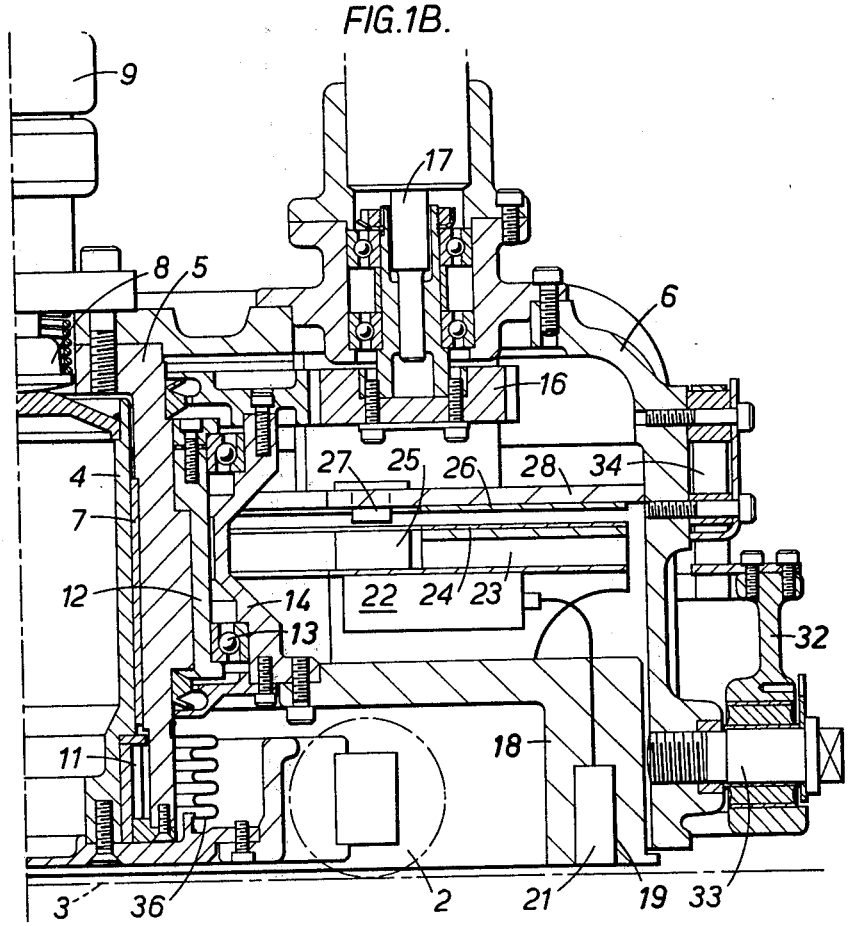

CARRIAGE MOUNTED APPARATUS FOR DETECTING SURFACE DEFECTS IN FLAT SURFACED METALLIC OBJECTS

The invention relates to surface inspection equipment and particularly, but not exclusively, relates to such equipment for detecting defects in the surface of steel billets.

According to the present invention there is provided apparatus for inspecting a flat surface of an elongate metallic object comprising a carriage mounted scanning head including a high-frequency eddy-current probe mounted on the periphery of a disc rotatable above the surface about an axis perpendicular thereto and about the periphery of the scanning head carriage.

Surface conditions detected by the inspection apparatus include surface defects, surface bruising and localised magnetic areas. The term "defect" as used herein is to be taken as including all such conditions.

More than one high-frequency eddy-current probe may be mounted on a periphery of the disc, the several probes being equi-spaced about the circumference of the disc. The or each probe may be housed in a recess set in the disc periphery. Signals representative of the condition of the surface under inspection may be transitted to signal processing equipment remote from the scanning head via an electronic module and transmitting aerial which rotate with and above the disc.

The housing of the scanning head may be mounted on the carriage through a resilient means which acts to bias the carriage away from the housing. The biasing means may comprise a spring-actuated plunger positioned between a shock absorber and a cylinder up-standing from the carriage, which is located within a complimentary-shaped bore of the housing.

Positioned about the circumference of the scanning head housing may be located a gimbal device which, in concert with the housing, operates to position the disc vertically above and parallel to the surface under inspection.

The disc is preferably driven by a flexible drive through an internally-mounted bearing housing comprising a rotor which supports the disc which in turn supports the electronic module and the transmitting aerial.

Preferably, the signals representative of the condition of the surface under inspection are processed in equipment similar or identical to that disclosed and claimed in our U.K. Pat. No. 1475517 or co-pending Application No. 2008259A.

The invention will now be described by way of example only with reference to the accompanying drawing in which FIGS. 1A and 1B are cross sections taken through apparatus in accordance with the invention.

The surface scanner illustrated in the drawings comprises a carriage (1) having rollers (2) which transverse the surface of a metal billet (3) under inspection. The carriage has secured to its upper surface an upstanding cylinder (4) which can slide within a complementary shaped, non-rotating bearing shaft (5) which forms part of a dish-shaped housing (6) of the scanner. A bush (7) is located between the opposed surfaces of the cylinder (4) and the shaft (5) to facilitate sliding movement of the cylinder (4) within the bearing shaft (5).

A spring-loaded plunger (8) is positioned between the closed upper end of the cylinder (4) and a shock absorber (9), and operates to urge the carriage (1) in a direction away from the shock absorber (9) and towards the surface of the billet (3). Splines (11) are located on the external face of the lower end of the cylinder (4) and engage complementary splines located on the non-rotating bearing shaft (5) to prevent rotation of the cylinder (4).

The external face of the shaft (5) supports the stator (12) of a bearing housing comprising two axially adjustable angular contact bearing races (13) and a rotor (14). The rotor (14) is driven through a gear wheel (15) which meshes with a pinion (16) connected to a flexible drive shaft (17) of an electric motor (not shown).

The rotor (14) supports a dish-shaped scanning disc (18) which encompasses the carriage (1) and includes recesses (19) which house high frequency energised eddy-current probes (21). The probes (21) are each connected to receive and transmit signals indicative of the condition of the surface over which they scan to electronic modules (22) carried on the underside of a rotating annulus (23) supported by the disc (18). Supported on the upper side of the annulus (23) are a transmitting aerial (24) and an array of pick-up coils (25) positioned respectively below a receiving aerial (26) and a ring of magnets (27) secured to the underside of a stationary annulus (28); the magnets (27) operate to induce electrical signals within the rotating pick-up coils (25) to power the probes (21).

The gear wheel (15) has an upstanding tooth (29) which passes below a pulse generator (31) located in the housing (6) to monitor continuously the angular position of the probes (21) as the scanning disc (18) rotates. Mounted about the periphery of the housing (6) (which acts as an inner gimbal) is an outer gimbal (32). The housing (6) and outer gimbal (32) are pivotably mounted on flexible bush pivots (33) below hairpin springs (34) to ensure that the scanning disc (18) maintains a required parallel attitude to the billet surface even when changes occur in the latter due to surface irregularities, billet bend and twist.

The ingress of dirt and other foreign bodies to the bearings (13) is prevented by annular dirt shields (35) and bellows (36).

The operation of the illustrated surface scanner will now be described. When the scanner is in its non-inspection mode, the carriage (1) is extended below the undersurface of the scanner due to the spring action of the plunger (8) acting on the end of the cylinder (4). In its inspection mode, the scanner is moved onto the front end of the billet surface to be inspected as the billet travels towards and below the scanner by a remotely-controlled mechanism (not shown) which may also support one or more additional scanners for inspecting other surfaces of the billet. As contact is made with the billet, the cylinder (4) is moved within the bore of the bearing shaft (5) until the carriage is located in the position illustrated in the drawing. Because the carriage rollers (2) are mounted inboard of the scanning disc (18) and probes (21), the entire length of the billet surface can be inspected.

As the scanning disc (18) is rotated by the drive shaft (17) through the rotor (14), the probes (21) continuously scan over the surface of the billet (3) and transmit signals representative of the scanned surface through the modules (22) and the aerials (24,26) to signal-processing equipment remote from the scanner. This processing equipment may be identical or similar to the equipment described and illustrated in our U.K. Pat. No. 1475517 and U.K. Pat. Application No. 2008259 A.

We claim:

1. Apparatus for inspecting a flat surface of an elongate metallic object which comprises:
   (a) a carriage operable to traverse the object surface to be inspected;
   (b) a rotor rotatably mounted on the carriage and coupled to a flexible drive such that it rotates about an axis perpendicular to the object surface;
   (c) a scanning disc attached to the rotor so as to rotate about the periphery of the carriage about an axis perpendicular to the object surface;
   (d) high frequency energized eddy-current probes located within recesses in the periphery of the scanning disc so that the probes scan the object surface at locations outboard of the carriage;
   (e) a housing for the scanning disc supported on the carriage; and,
   (f) a gimbal device positioned about the circumference of the housing and operable in concert with the housing to position the scanning disc vertically above and substantially parallel to the object surface to be inspected.

2. Apparatus as claimed in claim 1 further comprising an electronic module and transmitting aerial supported by and rotatable with the rotor, the electronic module and aerial operable to transmit signals representative of the surface under inspection to signal processing equipment remote from the scanning head.

* * * * *